United States Patent
Chronister

(10) Patent No.: US 10,018,034 B2
(45) Date of Patent: Jul. 10, 2018

(54) DENSITY MEASUREMENT USING A PIEZOELECTRIC SENSOR IN A NON-COMPRESSIBLE MEDIUM

(71) Applicant: Vernon Chronister, Claremore, OK (US)

(72) Inventor: Vernon Chronister, Claremore, OK (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 676 days.

(21) Appl. No.: 14/203,203

(22) Filed: Mar. 10, 2014

(65) Prior Publication Data
US 2015/0252667 A1 Sep. 10, 2015

(51) Int. Cl.
| | | |
|---|---|---|
| *E21B 47/06* | (2012.01) | |
| *G01N 9/00* | (2006.01) | |
| *E21B 47/10* | (2012.01) | |
| *E21B 43/12* | (2006.01) | |

(52) U.S. Cl.
CPC .............. *E21B 47/10* (2013.01); *E21B 43/12* (2013.01); *G01N 2009/006* (2013.01); *G01N 2203/0623* (2013.01)

(58) Field of Classification Search
CPC ..... G01N 2203/0623; G01N 2009/009; G01N 2009/006
See application file for complete search history.

(56) References Cited

U.S. PATENT DOCUMENTS

| | | | |
|---|---|---|---|
| 4,470,294 A | 9/1984 | Hamel | |
| 5,123,287 A | 6/1992 | Lew | |
| 6,301,973 B1 | 10/2001 | Smith | |
| 6,311,549 B1 * | 11/2001 | Thundat | G01N 9/002 |
| | | | 73/24.05 |
| 6,938,470 B2 | 9/2005 | DiFoggio et al. | |
| 8,453,507 B2 | 6/2013 | Ellson et al. | |
| 2002/0189323 A1 | 12/2002 | Francisco, Jr. | |
| 2005/0145019 A1 * | 7/2005 | Matsiev | G01N 9/002 |
| | | | 73/53.01 |
| 2007/0289740 A1 * | 12/2007 | Thigpen | E21B 37/06 |
| | | | 166/250.01 |

(Continued)

OTHER PUBLICATIONS

Allwright, D. 2002. The vibrating tuning fork fluid density tool. Report, Smith Institute, http://www.smithinst.ac.uk/projects/ESGI43/ESGI43-NanGall/index_html.*

(Continued)

*Primary Examiner* — Jennifer Simmons
(74) *Attorney, Agent, or Firm* — Cantor Colburn LLP

(57) ABSTRACT

A system, method and apparatus for determining a parameter of a fluid is disclosed. Measurements are obtained of a temperature of the fluid and a pressure of the fluid. A material is disposed in the fluid, and an actuator applies a stimulation pulse at a selected frequency to the material to generate an oscillation in the material. A measurement device measures a parameter of oscillation of the material in response to the stimulation pulse, the parameter of oscillation being affected by the fluid in which the material is disposed. A processor determines the parameter of the fluid from the measured parameter of the oscillation, the temperature measurement and the pressure measurement.

17 Claims, 4 Drawing Sheets

(56) References Cited

U.S. PATENT DOCUMENTS

2011/0166801 A1 7/2011 Cunningham et al.
2011/0219872 A1 9/2011 Hussain et al.

OTHER PUBLICATIONS

PCT International Search Report and Written Opinion; International Application No. PCT/US2015/014608; International Filing Date: Feb. 5, 2015; dated May 19, 2015; pp. 1-14.

* cited by examiner

DENSITY MEASUREMENT USING A PIEZOELECTRIC SENSOR IN A NON-COMPRESSIBLE MEDIUM

BACKGROUND OF THE DISCLOSURE

1. Field of the Disclosure

The present disclosure is related to measuring a fluid property and, in particular, to determining a fluid property based on an oscillation of a sensor disposed in the fluid.

2. Description of the Related Art

Production systems are used to obtain fluids form a reservoir found in a formation. A production system includes a member or tubular that is disposed in a borehole that penetrates the formation. Fluid from the formation flows into the member and is directed upward to the surface for processing. The flow of the fluid depends on various parameters of the fluid, such as its density, composition, viscosity, etc. These parameters can be altered, for instance, by addition of chemical additives to the fluid. There is therefore a need for determining a parameter of the fluid so as to determine a suitable action to take to change the parameter of the fluid.

SUMMARY OF THE DISCLOSURE

In one aspect the present disclosure provides a method of determining a parameter of a fluid, the method including: obtaining a measurement of a temperature of the fluid; obtaining a measurement of a pressure of the fluid; applying a stimulation pulse at a selected frequency to a sensor disposed in the fluid, determining a parameter of oscillation of the sensor in response to the stimulation pulse; and determining the parameter of the fluid from the determined parameter of the oscillation, the obtained measurement of the temperature and the obtained measurement of the pressure.

In another aspect, the present disclosure provides a system for determining a parameter of a fluid, the system including: a pressure sensor configured to obtain a measurement of a pressure of the fluid; a temperature sensor configured to obtain a measurement of a temperature of the fluid; a material disposed in the fluid, an actuator configured to apply a stimulation pulse at a selected frequency to the material to generate an oscillation in the material; a measurement device configured to measure a parameter of oscillation of the material in response to the stimulation pulse; and a processor configured to determine the parameter of the fluid from the measured parameter of the oscillation, the obtained measurement of the temperature and the obtained measurement of the pressure.

In yet another aspect, the present disclosure provides a production system, including: a member for providing flow of a fluid from a formation; a pressure sensor configured to obtain a measurement of a pressure of the fluid in the member; a temperature sensor configured to obtain a measurement of a temperature of the fluid in the member; a material disposed in the member and submerged in the fluid, an actuator configured to apply a stimulation pulse to the material to generate an oscillation in the material; a measurement device configured to measure a parameter of oscillation of the material in response to the stimulation pulse; and a processor configured to determine the parameter of the fluid from the measured parameter of the oscillation, the obtained measurement of the temperature and the obtained measurement of the pressure.

Examples of certain features of the apparatus and method disclosed herein are summarized rather broadly in order that the detailed description thereof that follows may be better understood. There are, of course, additional features of the apparatus and method disclosed hereinafter that will form the subject of the claims.

BRIEF DESCRIPTION OF THE DRAWINGS

For detailed understanding of the present disclosure, references should be made to the following detailed description, taken in conjunction with the accompanying drawings, in which like elements have been given like numerals and wherein.

DETAILED DESCRIPTION OF THE DISCLOSURE

Figure 1:
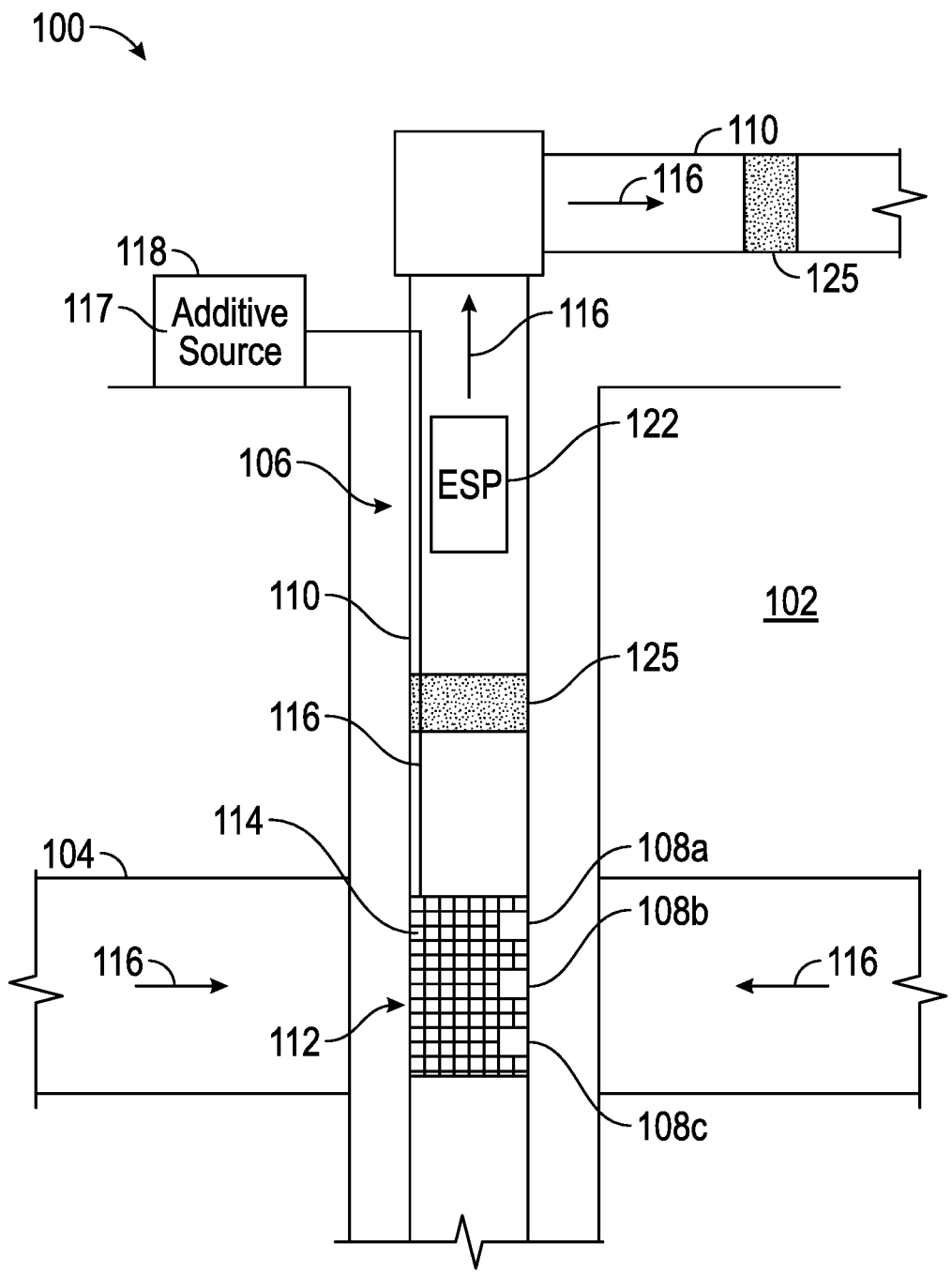
FIG. 1 shows an exemplary production system suitable for obtaining fluid from a formation in one embodiment of the present disclosure.

FIG. 1 shows an exemplary production system 100 suitable for obtaining fluid from a formation in one embodiment of the present disclosure. The production system 100 includes one or more production members 110 disposed in a borehole 106 penetrating a formation 102. The production members 110 may be tubular members joined to each other to form a production tubular for flow of fluid from the formation. In the illustration of FIG. 1, the borehole 106 is shown as a vertical borehole. However, the borehole 106 may also be a horizontal borehole or a horizontal section of a borehole 106. An inlet section 112 of the one or more production members 110 is placed proximate a reservoir 104 in the formation from which various formation fluids 116 may be extracted. The inlet section 112 may include a screen 114 that allows the formation fluid 116 to flow from the reservoir 104 into an interior section of the one or more production members 110 and up to the surface. An electrical submersible pump (ESP) 122 may be used to pump the fluid 116 in the production members 110 to the surface. The production system 100 further includes valves 108a, 108b, 108c for controlling a flow of formation fluid 116 from the reservoir 104 into an interior region of the production members 110. While only three valves are shown in FIG. 1 for illustrative purposes, production members 110 may include more than three valves in various embodiments and often includes from hundreds to thousands of valves. A capillary tube 116 may be used to provide chemical additives 117 from a chemical additive source 118. The chemical additives 117 may be used to alter a parameter of the formation fluid 116, such as a viscosity of the fluid 116, a density of the fluid 116, a chemical composition of the fluid 116, etc. in order to improve flow of the fluid 116 through the production system 100. In various embodiments, the one or more production members 110 may include a sensor section 125 suitable for determining one or more parameters of the fluid 116, such as a density of the fluid or a composition of the fluid, using the methods disclosed herein. The sensor section 125 may be located either at a downhole location or at a surface location, as illustrated in FIG. 1.

Figure 2:
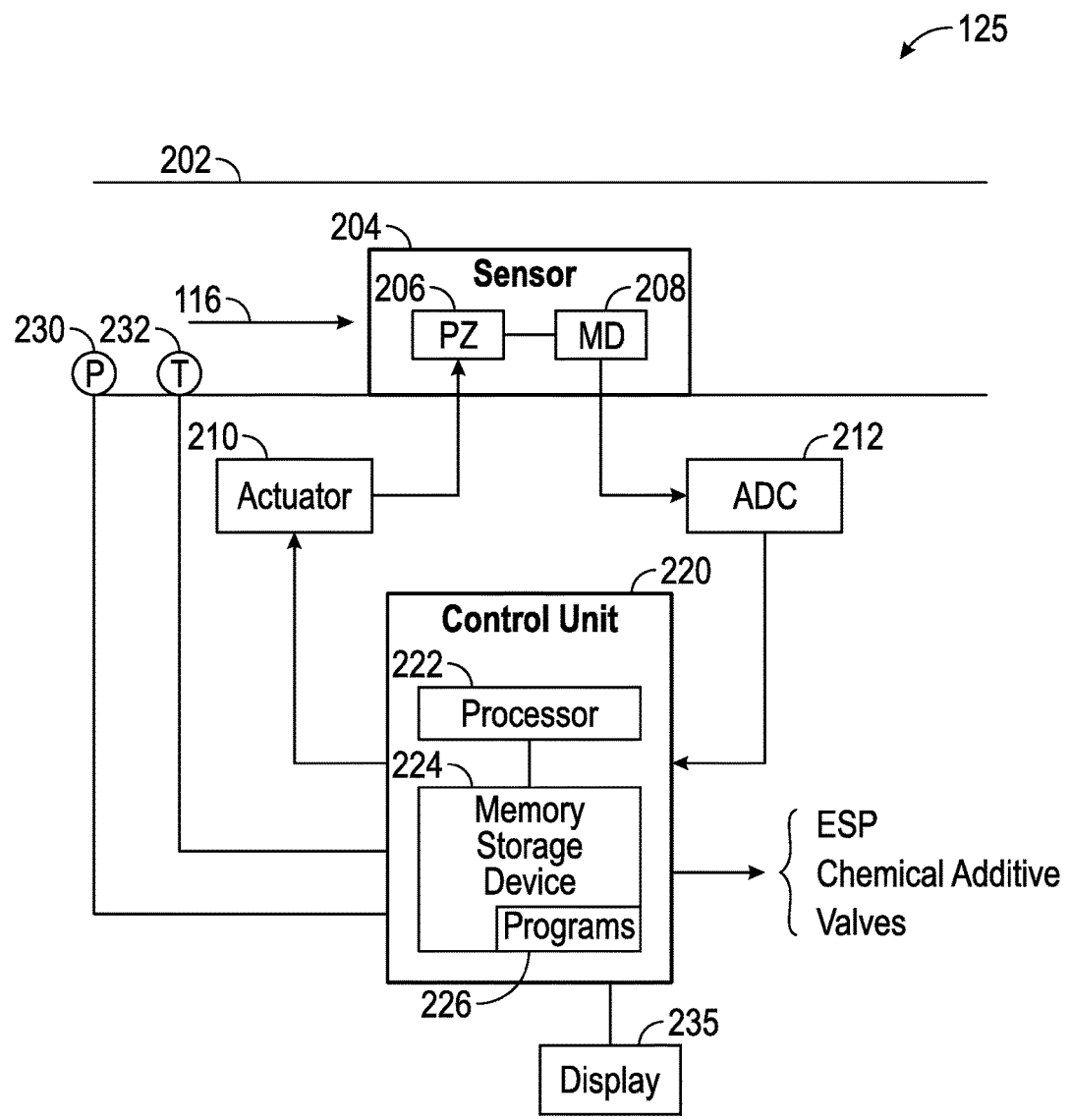
FIG. 2 shows a detailed view of the sensor section of the production system of FIG. 1.

FIG. 2 shows a detailed view of the sensor section 125 of the production system 100 of FIG. 1. The exemplary sensor section 125 includes a section 202 of the production members 110 that includes a sensor 204 therein. The sensor 204 is disposed within section 202 of the production string 110 and is submerged in the fluid 116 flowing through the section 202. The sensor 204 may include a piezoelectric material (PZ) 206 that has a self-resonance frequency. The piezoelectric material 206 may include, for example, quartz, silicon carbide, or any suitable material capable of self-resonance. The piezoelectric material 206 deforms when an electrical potential is applied to the piezoelectric material 206 or an electric current is passed through the piezoelectric material 206. Additionally, the piezoelectric material 206 responds to a deformation or change in its shape by generating an electrical current or voltage.

Sensor 204 is electrically coupled to an actuator 210. The actuator 210 may provide electrical simulation, mechanical stimulation or a combination thereof to the sensor 204. The actuator 210 may supply an electrical stimulation pulse to the piezoelectric material 206 in order to deform the piezoelectric material 206 away from its equilibrium or relaxed state. Once the stimulation pulse is removed, the piezoelectric material 206 relaxes back to its equilibrium state, generally oscillating as it does so and generating an electrical signal indicative of its oscillations. The oscillation of the piezoelectric material 206 is generally characterized by one or more parameters of the oscillation, such as an amplitude of the oscillation, a frequency of the oscillation, a decay rate of the oscillation, etc. The values of these parameters of oscillation are affected by the density of the fluid 116, and/or a composition of the fluid, such as whether the fluid includes water, oil, a water/oil mixture, etc. Therefore, the parameter of oscillation may be measured and used to determine a density and/or composition of the fluid 116. Sensor 204 further includes a measurement device (MD) 208. The measurement device 208 measures the electrical signals, such as current and/or voltage, generated by the oscillating piezoelectric material 206. The measurement device 208 sends the electrical signal to an analog-to-digital converter (ADC) 212 which converts the electrical signal to a digital format suitable for control unit 220.

Control unit 220 is coupled to the actuator 210 and controls a stimulation frequency provided by the actuator 210 to the piezoelectric material 206. Control unit 220 is further coupled to the ADC 212, receives electrical signals indicative of a parameter of oscillation of the piezoelectric material 206 from the ADC 212, and determines a parameter of the fluid 116 from the received electrical signals. The control unit 220 includes a processor 222 and a memory storage device 224 accessible to the processor 222. The memory storage device 224 may include any form of non-transitory storage medium such as a solid-state memory device, a read-only memory (ROM) or other suitable memory type. A set of programs 226 for performing the methods disclosed herein may be stored on the memory storage device 224 and may be accessible to the processor 222. The processor 222 may therefore access the programs 226 to, for example, control a stimulation pulse at the actuator 210, receive signals from the ADC 212 and determine from the received electrical signals a selected parameter of the fluid 116.

A pressure sensor 230 and a temperature sensor 232 may be disposed in the fluid 116. Pressure sensor 230 may provide a pressure measurement of the fluid 116 to control unit 220. Similarly, temperature sensor 232 may provide a temperature measurement of the fluid 116 to the control unit 220. The control unit 210 may determine the parameter of the fluid (e.g., density, composition) from the measured temperature, measured pressure of the fluid and a parameter of oscillation of the piezoelectric material 206.

In one embodiment, the processor 222 may locate a value of the parameter of the fluid 116 in a look-up table that relates the parameter of the fluid to temperature of the fluid, pressure of the fluid and the parameter of oscillation of the piezoelectric material 206 disposed in the fluid 116. A mass of the piezoelectric material 206 may also be used in the look-up table to determine the value of the parameter of the fluid 116. The look-up table may be assembled by operating the piezoelectric material over a suitable range of temperatures and pressures, in fluids of known fluid densities and/or compositions, using selected stimulation frequencies, etc. The look-up table may be assembled prior to disposing the piezoelectric material 206 in the fluid 116. The look-up table may be stored at the memory storage device 224.

In another embodiment, the processor 222 may perform calculations on equations relating the obtained measurement of temperature, the obtained measurement of pressure and the measured value of the parameter of oscillation to a density of the fluid. The calculations may further include the mass of the piezoelectric material 206 and other suitable parameters.

In various embodiments, the determined parameter of the fluid 116 may be stored to the memory storage device 224 and/or sent to a display 235. Alternatively, the determined parameter of the fluid 116 may be used to alter a production parameter of the production system 100, such as by altering a speed or frequency of the ESP 122, opening or closing a valve 114, altering a delivery rate of chemical additives 117 to the fluid 116, etc.

Figure 3:
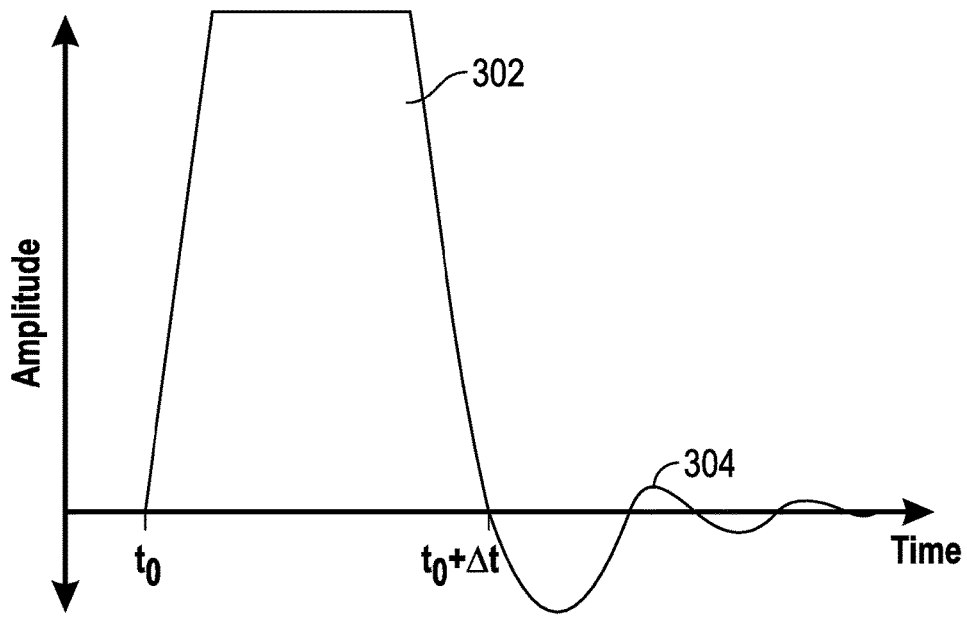
FIG. 3 shows an exemplary stimulation pulse that may be applied to a piezoelectric material and a corresponding relaxation signal generated by the piezoelectric material in response to the stimulation pulse.

FIG. 3 shows an exemplary stimulation pulse 302 that may be applied to the piezoelectric material 206 of sensor 204 and a corresponding relaxation signal 304 generated by the piezoelectric material 206 in response to the stimulation pulse 302. The stimulation pulse 302 may be used in order to deform the piezoelectric material 206 to a non-equilibrium state. Once the stimulation pulse 302 is removed, the piezoelectric material 206 relaxes back to its equilibrium state, thereby generating the oscillations of the relaxation signal 304. The relaxation signal 304 may appear as a decaying sine wave but may also be triangular wave, a half-sine wave, or a tapering voltage.

The stimulation pulse 302 may be a pulse beginning at time $t_0$ and ending at time $t_0+\Delta t$. A duration ($\Delta t$) of the stimulation pulse 302 may correspond to a selected period (and thus a frequency) for the corresponding relaxation signal 304. A long pulse may stimulate a low frequency oscillation in the piezoelectric material 206 and a short pulse may stimulation a high frequency oscillation in the piezoelectric material 206. The stimulation pulse 302 may have a fixed amplitude, as shown in FIG. 3 or a variable amplitude. The frequency of the stimulation pulse 302 may be selected based on the self-resonance frequency of the piezoelectric material 206. In various embodiments, the frequency of the stimulation pulse 302 may be selected so as to be sufficiently distinct or away from the self-resonance frequency of the piezoelectric material 206 so as to avoid or prevent generation of an oscillation at or near the self-resonance frequency of the piezoelectric material 206 (i.e., a resonant frequency oscillation).

The relaxation signal 304 represents a signal generated by the material 206 in response to the stimulation signal 302, once the stimulation pulse 302 has been removed. The parameters of the relaxation signal 304, i.e., the oscillation frequency of the relaxation signal 304, the amplitude of the relaxation signal 304, the decay rate of the relaxation signal 304, are affected by the frequency of the stimulation pulse 302, the mass of the piezoelectric material 206 and various parameters (i.e., temperature, pressure, density) of the fluid 116 in which the piezoelectric material 206 is disposed. Therefore, the parameters of oscillation of the relaxation signal 304 may be used to determine the parameter of the fluid 116.

Figure 4:
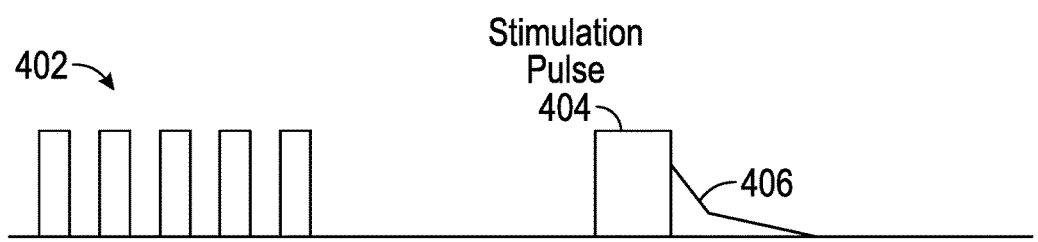
FIG. 4 shows a set of signals that may be applied to the piezoelectric material for determining a parameter of the fluid in one embodiment.

FIG. 4 shows a set of signals that may be applied to the piezoelectric material 206 for determining a parameter of the fluid in one embodiment. Before any measurements are made, a series of cleansing pulses 402 may be applied to the piezoelectric material 206 at the self-resonant frequency of the piezoelectric material 206. These pulses 402 cause the piezoelectric material 206 to dislodge any materials that may have accumulated on the piezoelectric material 206. Material accumulation on the piezoelectric material 204 alters the mass of the piezoelectric material 206 from its recorded value and therefore introduces error into calculations that determine the various parameters of the fluid. Dislodging the accumulated material reduces this mass error.

After dislodging accumulated material from the piezoelectric material 206, and waiting a selected amount of time for sufficient diminution of the oscillations of sensor 206 due to the cleansing pulses 402, a stimulation pulse 404 is applied to the piezoelectric material 206 at a frequency distinct form the self-resonance frequency of the piezoelectric material 206. A parameter of oscillation of the relaxation signal 406 is then measured and used to determine the parameter of the fluid 116. In closer detail, the relaxation signal 406 has a wave shape such as shown in the relaxation signal 304 of FIG. 3.

The self-resonance frequency of the piezoelectric material 206 may be determined throughout a range of temperatures and pressures during a calibration stage prior to applying the stimulation pulse 404. The self-resonance frequency may be stored in memory storage device 224 and may be used to select the frequency of the stimulation pulse 404.

Figure 5:
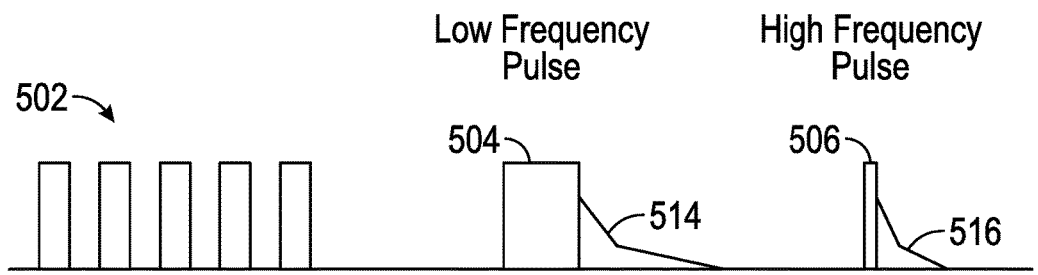
FIG. 5 shows a set of signals that may be applied to the piezoelectric material for determining the parameter of the fluid in another embodiment.

FIG. 5 shows a set of signals that may be applied to the piezoelectric material 206 for determining a parameter of the fluid in another embodiment. Cleansing pulses 502 are applied to the piezoelectric material 206 to dislodge accumulated materials from the sensors 206. After a waiting a selected time for sufficient diminution of the oscillations of the sensor 204 due to the cleaning pulses 502, a set of stimulations pulses are applied to the piezoelectric material 206. Two stimulation pulses 504 and 506 may be applied to the piezoelectric material 206. The first stimulation pulse 504 and may be a low frequency pulse having a frequency that is less than a self-resonance frequency of the piezoelectric material 206. The second stimulation pulse 506 may be a high frequency pulse having a frequency that is greater than the self-resonance frequency of the piezoelectric material 206. In one embodiment, the frequency of the first stimulation pulse 504 is about five octaves below the self-resonance frequency and the frequency of the second stimulation pulse 506 is about five octaves above the self-resonance frequency of the piezoelectric material 206. In various embodiments, the high and low stimulation frequencies are selected so as to be distinct from the self-resonance frequency of the piezoelectric material 206 so as not to induce a resonance in the piezoelectric material 206.

The first (lower frequency) stimulation pulse 504 is applied to the piezoelectric material 206 and the parameters of oscillation of the corresponding relaxation signal 514 are measured and/or sampled. The duration of the stimulation pulse 504 is inversely proportional to the frequency of the stimulation pulse 504. Then the second (high frequency) stimulation pulse 506 is applied to the piezoelectric material 206 and the parameters of oscillation of the corresponding relaxation signal 516 are measured. The duration of the stimulation pulse 506 is inversely proportional to the frequency of the stimulation pulse 505. In closer detail, the relaxation signals 514 and 516 may have wave shapes such as shown in the relaxation signal 304 of FIG. 3. The parameters of the first relaxation signal 514 may then be used to determine a first value of the parameter of the fluid 116, and the second relaxation signal 416 may be used to determine a second value of the parameter of the fluid 116. These values may be compared to each other to obtain an average value, interpolated value, or other determined value for the parameter of the fluid 116.

Figure 6:
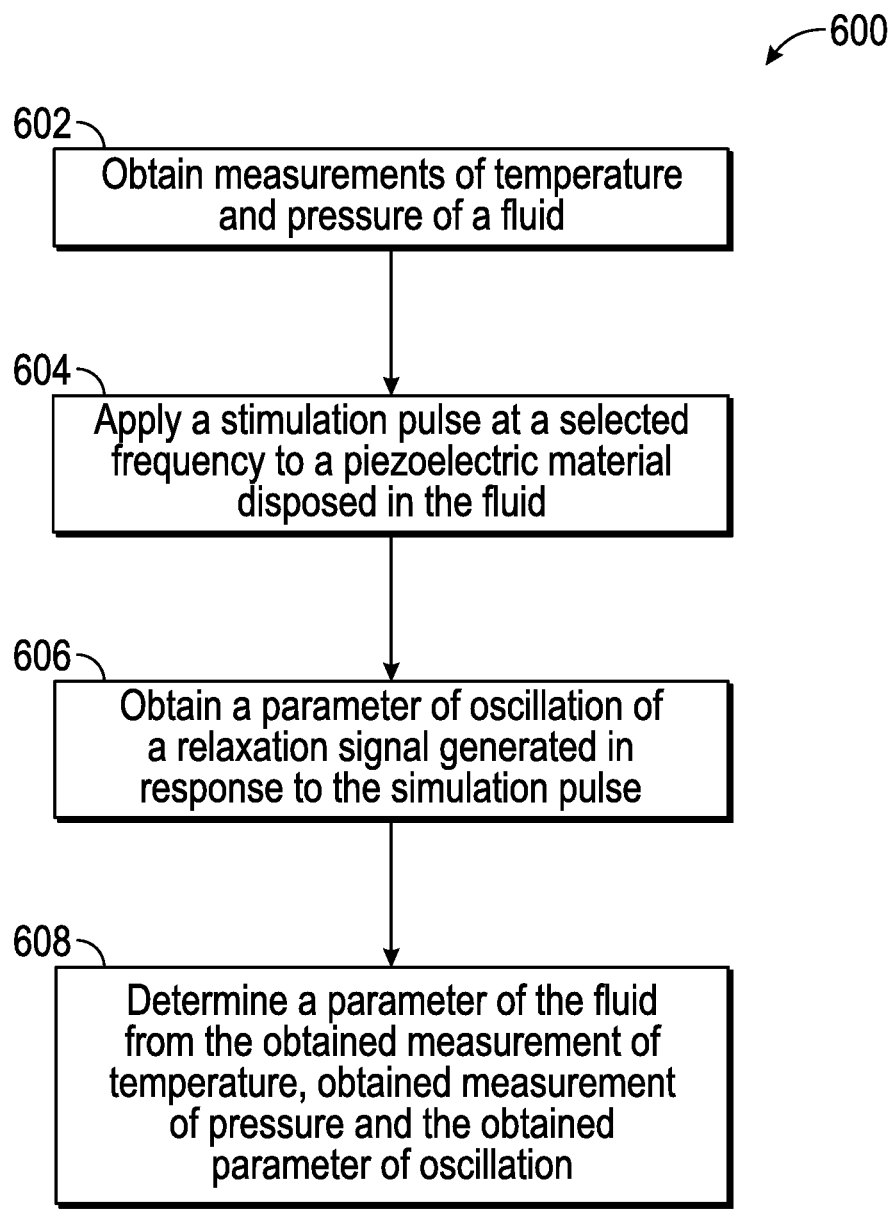
FIG. 6 shows a flowchart illustrating an exemplary method of determining a parameter of a fluid in one embodiment of the present invention.

FIG. 6 shows a flowchart 600 illustrating an exemplary method of determining a parameter of a fluid in one embodiment of the present invention. In box 602, a temperature measurement of the fluid and a pressure temperature of the fluid are obtained. In box 604, a stimulation pulse having a selected frequency is applied to a piezoelectric material disposed in the fluid. The selected frequency of the stimulation pulse is sufficiently distinct from the resonant frequency of the piezoelectric material so as to avoid or reduce generation of an oscillation at a resonant frequency of the piezoelectric material. In box 606, a parameter of oscillation of a relaxation signal generated in response to the stimulation pulse is measured. In box 608, the parameter of oscillation, the measured temperature and the measured pressure are used to determine a parameter of the fluid such as density and/or composition of the fluid.

The determined parameter of the fluid may then be used in altering a parameter of the production process, such as altering a speed or frequency of the electric submergible pump (122, FIG. 1), opening and/or closing valves (118a-c, FIG. 1) and/or changing a delivery rate of chemical additives (117, FIG. 1), among others. At a fixed temperature or pressure, the voltage and current levels will change as the different fluids with different densities come into contact with the piezoelectric material 206. The changes to the parameters of the production process may be performed in real-time in reaction to various changes in the parameters of the fluid. In various embodiments, the piezoelectric material may be used to determine the temperature of the fluid as well as to oscillation in response to the stimulation signal.

Therefore, in one aspect the present disclosure provides a method of determining a parameter of a fluid, the method including: obtaining a measurement of a temperature of the fluid; obtaining a measurement of a pressure of the fluid; applying a stimulation pulse at a selected frequency to a sensor disposed in the fluid, determining a parameter of oscillation of the sensor in response to the stimulation pulse; and determining the parameter of the fluid from the determined parameter of the oscillation, the obtained measurement of the temperature and the obtained measurement of the pressure. The selected frequency is a frequency that is distinct from a self-resonance frequency of the sensor. In one embodiment, applying the stimulation pulse includes applying a low-frequency stimulation pulse and a high-frequency stimulation pulse, wherein the frequency of the low-frequency stimulation is less than a self-resonance frequency of the sensor and the frequency of the high-frequency stimulation pulse is greater than the self-resonance frequency of the sensor. The parameter of oscillation may include a frequency of the oscillation, an amplitude of the oscillation, and/or a decay rate of the oscillation. In an embodiment in which the sensor includes a piezoelectric material, obtaining the parameter of oscillation includes measuring an electrical signal generated by oscillation of the piezoelectric material in response to the applied stimulation pulse. The parameter of the fluid may include a density of the fluid and/or a composition of the fluid. The parameter of the fluid may be determined by: (i) using the determined parameter of the oscillation, the obtained measurement of the temperature and the obtained measurement of the pressure in a look-up table; or (ii) performing a calculation using the determined parameter of the oscillation, the obtained measurement of the temperature and the obtained measurement of the pressure. In various embodiments, the fluid is a production fluid obtained from a formation.

In another aspect, the present disclosure provides a system for determining a parameter of a fluid, the system including: a pressure sensor configured to obtain a measurement of a pressure of the fluid; a temperature sensor configured to obtain a measurement of a temperature of the fluid; a material disposed in the fluid, an actuator configured to apply a stimulation pulse at a selected frequency to the material to generate an oscillation in the material; a measurement device configured to measure a parameter of oscillation of the material in response to the stimulation pulse; and a processor configured to determine the parameter of the fluid from the measured parameter of the oscillation, the obtained measurement of the temperature and the obtained measurement of the pressure. The actuator may apply the stimulation pulse at a frequency that substantially avoids generating an oscillation of the material at a self-resonance frequency of the material. In one embodiment, the actuator applies a low-frequency stimulation pulse to the material having a frequency less than the self-resonance frequency of the material and a high-frequency stimulation pulse to the material having a frequency of the greater than the self-resonance frequency of the material. The parameter of oscillation may include at least one of: (i) a frequency of the oscillation; (ii) an amplitude of the oscillation; and (iii) a decay rate of the oscillation. The material may be a piezoelectric material and the measurement device may measure an electrical signal generated by oscillation of the piezoelectric material. The parameter of the fluid may include at least one of: (i) a density of the fluid; and (ii) a composition of the fluid. The processor may determine the parameter of the fluid by performing one selected from the group consisting of: (i) using the determined parameter of the oscillation, the obtained measurement of the temperature and the obtained measurement of the pressure in a look-up table; and (ii) performing a calculation using the measured parameter of the oscillation, the obtained measurement of the temperature and the obtained measurement of the pressure. The fluid may be a production fluid obtained from a formation.

In yet another aspect, the present disclosure provides a production system, including: a member for providing flow of a fluid from a formation; a pressure sensor configured to obtain a measurement of a pressure of the fluid in the member; a temperature sensor configured to obtain a measurement of a temperature of the fluid in the member; a material disposed in the member and submerged in the fluid, an actuator configured to apply a stimulation pulse to the material to generate an oscillation in the material; a measurement device configured to measure a parameter of oscillation of the material in response to the stimulation pulse; and a processor configured to determine the parameter of the fluid from the measured parameter of the oscillation, the obtained measurement of the temperature and the obtained measurement of the pressure. The actuator may apply the stimulation pulse at a frequency that substantially avoids generation of an oscillation of the material at a self-resonance frequency of the material. In one embodiment, the actuator applies a low-frequency stimulation pulse to the material having a frequency less than the self-resonance frequency of the material and a high-frequency stimulation pulse to the material having a frequency of the greater than the self-resonance frequency of the material. The processor may be configured to determine the parameter of the fluid by performing one selected from the group consisting of: (i) using the determined parameter of the oscillation, the obtained measurement of the temperature and the obtained measurement of the pressure in a look-up table; and (ii) performing a calculation using the measured parameter of the oscillation, the obtained measurement of the temperature and the obtained measurement of the pressure.

While the foregoing disclosure is directed to the certain exemplary embodiments of the disclosure, various modifications will be apparent to those skilled in the art. It is intended that all variations within the scope and spirit of the appended claims be embraced by the foregoing disclosure.

The invention claimed is:

1. A method of operating a production system, comprising:
    obtaining a measurement of a temperature of the fluid;
    obtaining a measurement of a pressure of the fluid;
    determining a self-resonance frequency of a sensor at the temperature and pressure of the fluid;
    selecting a stimulation frequency for a stimulation pulse that avoids the self-resonance frequency, wherein the stimulation frequency is inversely proportional to a duration of the stimulation pulse;
    applying the stimulation pulse to the sensor disposed in the fluid to deform the sensor from an equilibrium state;
    removing the stimulation pulse from the sensor to allow the sensor to relax back to its equilibrium state wherein the stimulation frequency is selected to avoid a self-resonance frequency of the sensor by about 5 octaves;
    determining a parameter of oscillation of the relaxation of the sensor;
    determining the parameter of the fluid from the determined parameter of the oscillation, the obtained measurement of the temperature and the obtained measurement of the pressure; and
    changing the parameter of the fluid to improve a flow of the fluid in the production system.

2. The method of claim 1, wherein applying the stimulation pulse further comprises applying a low-frequency stimulation pulse and a high-frequency stimulation pulse, wherein the frequency of the low-frequency stimulation is less than a self-resonance frequency of the sensor and the frequency of the high-frequency stimulation pulse is greater than the self-resonance frequency of the sensor.

3. The method of claim 1, wherein the parameter of oscillation further comprises at least one of: (i) a frequency of the oscillation; (ii) an amplitude of the oscillation; and (iii) a decay rate of the oscillation.

4. The method of claim 1, wherein the sensor includes a piezoelectric material and obtaining the parameter of oscillation further comprises measuring an electrical signal generated by oscillation of the piezoelectric material in response to the applied stimulation pulse.

5. The method of claim 1, wherein the parameter of the fluid further comprises at least one of: (i) a density of the fluid; and (ii) a composition of the fluid.

6. The method of claim 1, further comprising determining the parameter of the fluid by performing one selected from the group consisting of: (i) using the determined parameter of the oscillation, the obtained measurement of the temperature and the obtained measurement of the pressure in a look-up table; and (ii) performing a calculation using the determined parameter of the oscillation, the obtained measurement of the temperature and the obtained measurement of the pressure.

7. The method of claim 1, wherein the fluid is a production fluid obtained from a formation.

8. A production system, comprising:
a pressure sensor configured to obtain a measurement of a pressure of a fluid;
a temperature sensor configured to obtain a measurement of a temperature of the fluid;
a material disposed in the fluid,
an actuator configured to apply a stimulation pulse to the material to deform the material from an equilibrium state and to remove the stimulation pulse from the material to allow the material to relax back to its equilibrium state, wherein a frequency of the stimulation pulse is inversely proportional to a duration of the stimulation pulse and is selected to avoid a self-resonance frequency in the material by about 5 octaves;
a measurement device configured to measure a parameter of oscillation of the relaxation of the material; and
a processor configured to:
determine the self-resonance frequency of the material at the temperature and pressure of the fluid,
select the frequency of the stimulation pulse to avoid the self-resonance frequency,
control the actuator to apply the stimulation pulse to the material,
determine the parameter of the fluid from the measured parameter of the oscillation, the obtained measurement of the temperature and the obtained measurement of the pressure and change a parameter of the production system to correspond to the parameter of the fluid, and
change the parameter of the fluid to improve a flow of the fluid in the production system.

9. The system of claim 8, wherein the actuator is configured to apply a low-frequency stimulation pulse to the material having a frequency less than the self-resonance frequency of the material and a high-frequency stimulation pulse to the material having a frequency of the greater than the self-resonance frequency of the material.

10. The system of claim 8, wherein the parameter of oscillation further comprises at least one of: (i) a frequency of the oscillation; (ii) an amplitude of the oscillation; and (iii) a decay rate of the oscillation.

11. The system of claim 8, wherein the material is a piezoelectric material and the measurement device is configured to measure an electrical signal generated by oscillation of the piezoelectric material.

12. The system of claim 8, wherein the parameter of the fluid further comprises at least one of: (i) a density of the fluid; and (ii) a composition of the fluid.

13. The system of claim 8, wherein the processor is further configured to determine the parameter of the fluid by performing one selected from the group consisting of: (i) using the determined parameter of the oscillation, the obtained measurement of the temperature and the obtained measurement of the pressure in a look-up table; and (ii) performing a calculation using the measured parameter of the oscillation, the obtained measurement of the temperature and the obtained measurement of the pressure.

14. The system of claim 8, wherein the fluid is a production fluid obtained from a formation.

15. A production system, comprising:
a member for providing flow of a fluid from a formation;
a pressure sensor configured to obtain a measurement of a pressure of the fluid in the member;
a temperature sensor configured to obtain a measurement of a temperature of the fluid in the member;
a material disposed in the member and submerged in the fluid,
an actuator configured to apply a stimulation pulse to the material to deform the material from an equilibrium state and remove the stimulation pulse from the sensor to allow the sensor to relax back to its equilibrium state, wherein a frequency of the stimulation pulse is inversely proportional to a duration of the stimulation pulse and is selected to avoid a self-resonance frequency in the material by about 5 octaves;
a measurement device configured to measure a parameter of oscillation of the relaxation of the material; and
a processor configured to:
determine the self-resonance frequency of the material at the temperature and pressure of the fluid,
select the frequency of the stimulation pulse to avoid the self-resonance frequency,
control the actuator to apply the stimulation pulse to the material,
determine the parameter of the fluid from the measured parameter of the oscillation, the obtained measurement of the temperature and the obtained measurement of the pressure and change a parameter of the production system to correspond to the parameter of the fluid, and
change the parameter of the fluid to improve a flow of the fluid in the production system.

16. The production system of claim 15, wherein the actuator is configured to apply a low-frequency stimulation pulse to the material having a frequency less than the self-resonance frequency of the material and a high-frequency stimulation pulse to the material having a frequency of the greater than the self-resonance frequency of the sensor.

17. The production system of claim 15, wherein the processor is further configured to determine the parameter of the fluid by performing one selected from the group consisting of: (i) using the determined parameter of the oscillation, the obtained measurement of the temperature and the obtained measurement of the pressure in a look-up table; and (ii) performing a calculation using the measured parameter of the oscillation, the obtained measurement of the temperature and the obtained measurement of the pressure.

* * * * *